United States Patent [19]

Nishihara

[11] Patent Number: 4,847,694

[45] Date of Patent: Jul. 11, 1989

[54] PICTURE ARCHIVING AND COMMUNICATION SYSTEM IN WHICH IMAGE DATA PRODUCED AT VARIOUS LOCATIONS IS STORED IN DATA BASES AT VARIOUS LOCATIONS IN ACCORDANCE WITH LISTS OF IMAGE ID DATA IN THE DATA BASES

[75] Inventor: Eitaro Nishihara, Ootawara, Japan

[73] Assignee: Kabushiki Kaisha Toshiba, Kawasaki, Japan

[21] Appl. No.: 127,499

[22] Filed: Dec. 1, 1987

[30] Foreign Application Priority Data

Dec. 3, 1986 [JP] Japan .................. 61-286589

[51] Int. Cl.$^4$ ................. H04N 1/32; H04N 1/00; H04N 1/40
[52] U.S. Cl. ..................... 358/434; 358/448
[58] Field of Search .......... 358/257, 285, 293, 294, 358/280, 256 (U.S. only)

[56] References Cited

U.S. PATENT DOCUMENTS

| | | | |
|---|---|---|---|
| 4,437,127 | 3/1984 | Hirose | 358/257 |
| 4,591,922 | 5/1986 | Takano et al. | 358/257 |
| 4,604,653 | 8/1986 | Shimizu | 358/257 |
| 4,727,435 | 2/1988 | Otani et al. | 358/257 |
| 4,748,511 | 5/1988 | Nichols et al. | 358/256 |
| 4,768,099 | 8/1988 | Mukai | 358/257 |

FOREIGN PATENT DOCUMENTS

| | | |
|---|---|---|
| 3534065 | 4/1986 | Fed. Rep. of Germany . |
| 60-94575 | 5/1985 | Japan .................. 358/257 |
| 2165069 | 4/1986 | United Kingdom . |

*Primary Examiner*—James J. Groody
*Assistant Examiner*—Randall Svihla
*Attorney, Agent, or Firm*—Oblon, Spivak, McClelland, Maier & Neustadt

[57] ABSTRACT

A picture archiving and communication system comprises an image data output section, a terminal station, and a plurality of data bases. The image data output section produces diagnostic image data in accordance with examination requests made at a plurality of diagnosis departments, and outputs the diagnostic image data together with appendant data (which includes destination data indicating where the image data should be sent). From the terminal station are entered specific data used for specifying the image data produced by the image data output section, and destination data representing where the image data should be sent. The data bases are located at various diagnosis departments. On the basis of the data entered from the terminal station, a register list is prepared at each of the data bases, and the appendant data supplied from the image data output section is collated with the data recorded in the register list. In accordance with the results of the collation, image data is selectively stored in the data bases.

17 Claims, 6 Drawing Sheets

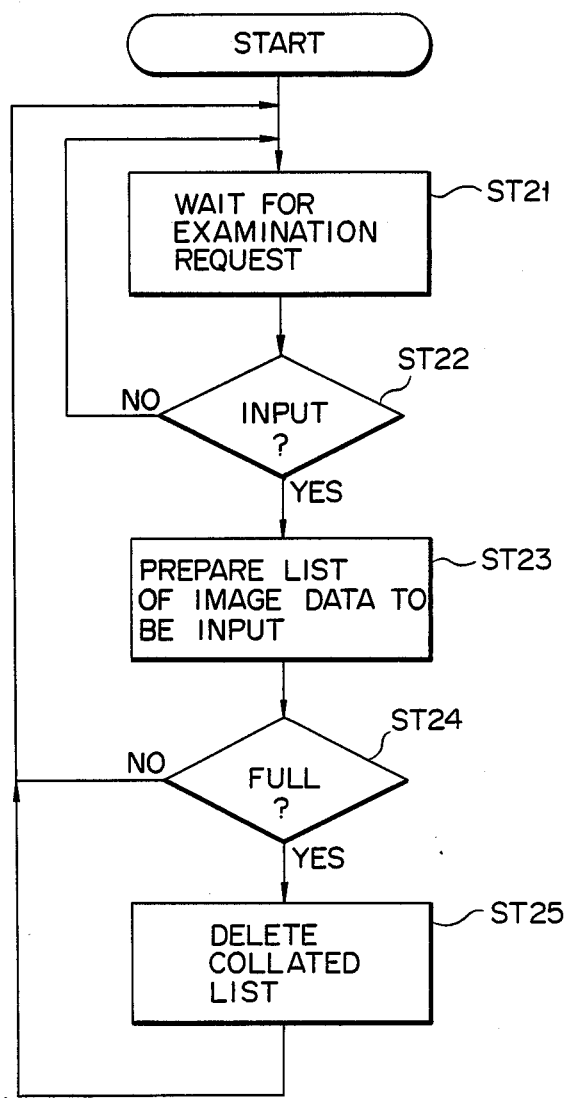
F I G. 2

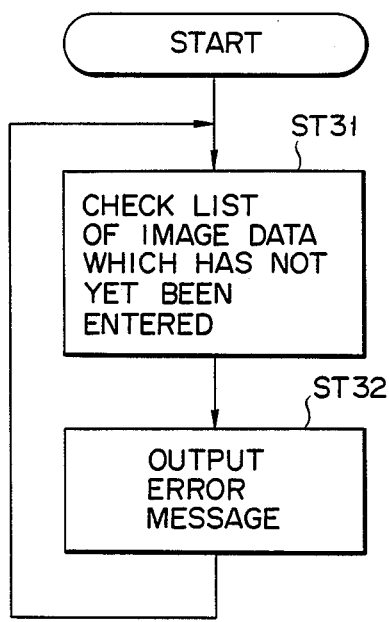
F I G. 3
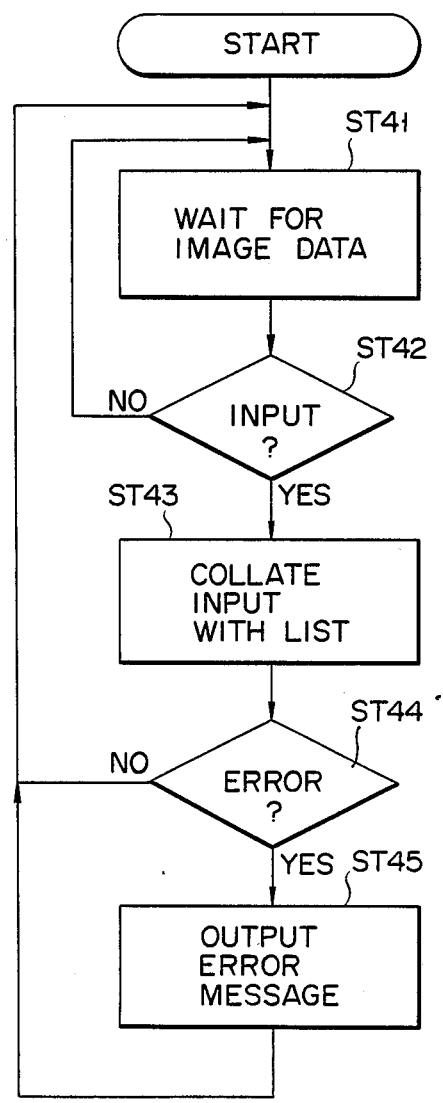
F I G. 4

| DATE OF REQUEST | PATIENT | ID | MODALITY | LOCATION OF EXAMINATION | DOCTOR IN CHARGE |
|---|---|---|---|---|---|
| | | | | | |
| | | | | | |
| | | | | | |
| | | | | | |
| | | | | | |

F I G. 5

PICTURE ARCHIVING AND COMMUNICATION SYSTEM IN WHICH IMAGE DATA PRODUCED AT VARIOUS LOCATIONS IS STORED IN DATA BASES AT VARIOUS LOCATIONS IN ACCORDANCE WITH LISTS OF IMAGE ID DATA IN THE DATA BASES

BACKGROUND OF THE INVENTION

The present invention relates to a picture archiving and communication system (PACS) which stores image data, produced by diagnosis apparatuses, into a plurality of data management devices (hereinafter referred to as "data bases") and administers the image data stored therein.

General hospital has a section for diagnosis, where a clinician performs a diagnosis of a patient, and a department for examination, where a specialist or a medical technician examines a patient by use of examination equipment. The internal medicine section, the surgery section, and the otolaryngology section are examples of the former type section, while the radiology department is an example of the latter. When performing a diagnosis, the clinician may sometimes judge that a diagnostic image of a patient is necessary for an accurate diagnosis to be arrived at. In such a case, the clinician fills in an examination request form, and asks the patient to proceed to, for example, the radiology department, (e.g., radiology department) for X-ray examination. In this examination (radiology) department, an X-ray examination is performed to the patient in accordance with the clinician's requests. Following the X-ray examination, the resultant X-ray image is returned to the clinician, together with the examination request form, and usually with the diagnostic reports of the image.

Recently, a synthetic diagnostic judgment system such as PACS has been developed, wherein the above examination procedures are controlled by computer. According to this system, image data, which is produced by various types of examination devices (also referred to as modalities), is transmitted to a data base. A terminal station is provided for each examination device, and codes used for identifying the image data (ID code) and codes representing the related diagnosis sections are entered from the terminal station at the same time as the image data is transmitted. These codes are supplied also sent to the data base, together with the image data. At the data base, therefore, image data is recorded and administered each time it is sent from the examination devices.

However, the above system may be faced with a problem, particularly if it includes a plurality of data bases. Assume that a wrong code is mistakenly entered from a terminal station to the system. In this case, the image data will be sent to and stored in an inappropriate data base. The occurrence of such a mistake cannot be detected in the above system.

In the above system, image data is stored in a data base, in response to a command supplied from an examination device. In other words, the storing of the image data into the data base is performed under the control of the examination device on the terminal. Therefore, the data base cannot identify the type of the image data until it actually receives the image data. Since all image data supplied from the examination device is recorded in the data base, it is probable that image data will be undesirably stored in the data base. In addition, even if the data base is not supplied with image data which it should receive, the data base cannot recognize the occurrence of this situation.

SUMMARY OF THE INVENTION

It is accordingly the object of the present invention to provide a picture archiving and communication system which enables a data base to control both image data which is mistakenly supplied to it and image data which it should receive but has not yet reached it.

To achieve this object, the picture archiving and communication system of the present invention comprises:
- at least one data output section which outputs image data and its appendant data, the appendent data including specific data used for specifying or identifying the image data and designation data representing where the image data should be sent;
- at least one terminal station by which specific data used for specifying the image data and the designation data are entered beforehand; and
- at least one data base, which includes means for preparing a register list on the basis of the specific data and designation data entered from the terminal station.

BRIEF DESCRIPTION OF THE DRAWINGS

FIGS. 2 through 4 are flow charts for illustrating the operation of the system shown in FIG. 1;

FIG. 5 shows a register list prepared by a data base of the system;

DETAILED DESCRIPTION OF THE PREFERRED EMBODIMENTS

Figure 1:
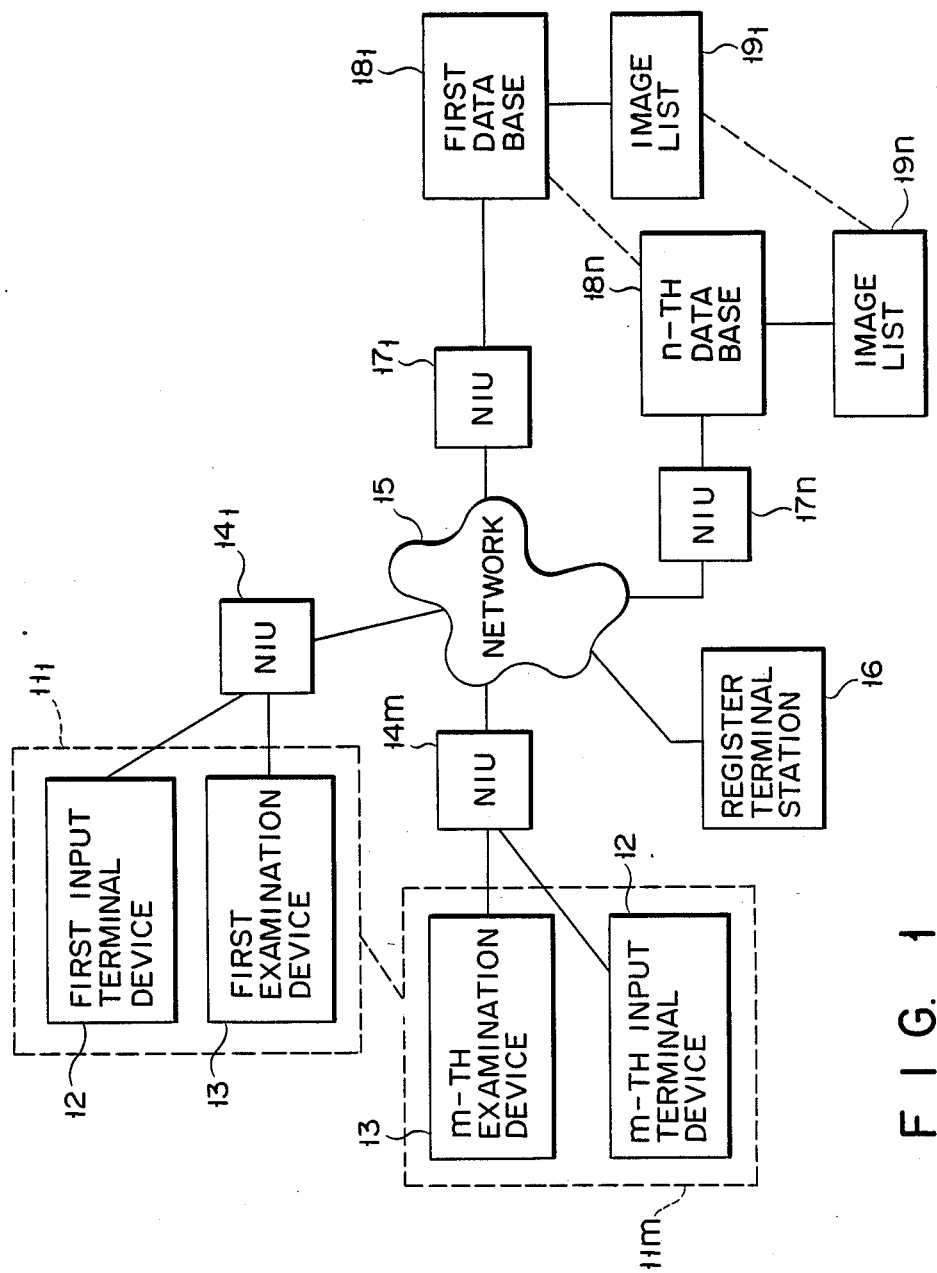
FIG. 1 illustrates the construction of a picture archiving and communication system according to one embodiment of the present invention.

FIG. 1 illustrates an off-line picture archiving and communication system according to one embodiment of the present invention. Referring to FIG. 1, a plurality of image data output sections $11_l$–$11_m$, which output image data about a patient, are located at the respective examination departments. Each of the image data output sections comprises input terminal device 12 and examination device 13. Input terminal device 12 is used to enter various types of data associated with the diagnostic image of a patient, namely, an image identification code, patient name, a modality, the location of examination, the name of the clinician in charge, etc. Examination device 13 includes an imaging device, such as an X-ray photography device, an ultrasonic imaging device, or an NMR imaging device.

Image data output sections $11_l$–$11_m$ are connected to network 15 by means of respective network interface units $14_l$–$14_m$. Network 15 is connected to register terminal station 16, as well as to a plurality of data bases $18_l$–$18_n$, by means of respective network interface units $17_l$–$17_n$. Data bases $18_l$–$18_n$ are arranged in various diagnosis sections of a hospital, such as the internal medicine section, and the surgery section and so forth.

Register terminal station 16 is used for entering data which can identify image data output from image data output sections $11_l$–$11_m$. For example, at least one of the appendant data and the destination data are entered.

Image register lists ($19_1$–$19_n$) are prepared by data bases $18_1$–$18_n$ respectively. Each of these lists includes a record of the appendant data entered from register terminal station 16 such that the appendant data is associated with the image data stored in the corresponding data base.

The operation of the above picture archiving and communication system will now be described, with reference to the flow charts shown in FIGS. 2-4.

First of all, an image register list is prepared according to the procedures shown in the flow chart in FIG. 2. Before the examination, the clinician in charge of a patient fills in an examination request form, as mentioned above. On the basis of this form, the operator enters the appendant data necessary for the preparations of the list by use of register terminal station 16. Register terminal station 16 is located at the department where examination request forms are collected.

Referring to the flow chart shown in FIG. 2, register terminal station 16 waits for an examination request (ST21) after starting the system. If there is an examination request, the operator enters appendant data (namely, the date of request, the name of the patient, an ID code, a modality, the location of examination, and the name of the clinician in charge) from register terminal station 16 (ST22). The entered data is sent to data base $18_1$–$18_n$, via network 15 and network interface units $17_1$–$17_n$. When the operator enters the appendant data from terminal station 16, he also enters a code representing the diagnosis department from which the examination request is supplied. By entering this code, the data base to which the entered data is to be sent is determined.

When the appendant data is supplied to data base section $18_l$, for example, it is transferred to image list memory $19_l$, so as to prepare an image register list such as that shown in FIG. 5. After the appendant data is thus stored in list memory $19_l$, a check is made as to whether or not memory $19_l$ is full (ST24). If memory $19_l$ is already storing a large amount of appendant data and is determined as being full, the data which has already been collated (the collation being performed according to the flow chart shown in FIG. 4) is deleted from the list (ST25). After the deletion of the collated data, the flow returns to ST21.

Image data is input simultaneous with the preparation of the image register list in the above fashion. When a patient comes to the examiaation department with an examination request form, the appendant data (e.g., an image ID, the name of the patient, a patient ID, a modality, the location of examination, the name of the clinician in charge, etc.) and the destination data (which represents the diagnosis department from which the examination request originated) are entered from input terminal 12, on the basis of the data in the examination request form. Then, the relevant area of the patent is photographed by use of examination device 13. The image data thus obtained is supplied to network 15 via network interface units $14_1$–$14_m$, along with the appendant data entered from input terminal 12. From network 15, the image data and the appendant data are supplied to the appropriate one of data base sections $18_1$–$18_n$ via the corresponding one of network interface unit $17_1$–$17_n$.

When both the image data and the appendant data are input to data base $18_l$, for example, the input appendant data is collated with the appendant data recorded in image list $19_l$. If both sets of data are in agreement, the input image data is recorded at data base $18_l$.

The above-mentioned operation is performed when there is no problem regarding the recording of the image data indicated in the image list. The flow chart shown in FIG. 3 illustrates the method for coping with the case where the image data indicated in the image list does not reach a data base. This situation occurs if a patient does not have himself photographed at the examination department, after the clinician has made out an examination request form, or if photographed image data has not been transmitted from the examination department, for some reason or other. According to the flow chart shown in FIG. 3, a check is made to determine whether image list memory $19_l$ contains a list whose corresponding image data has not yet been input (ST31). If image list memory $19_l$ contains such a list, an error message is output (ST32). On the basis of this error message, a check is made to determine why the image data corresponding to the list has not been input.

FIG. 4 shows a flow chart illustrating the method for coping with the case where image data is mistakenly supplied to an inappropriate data base. According to this flow chart, the data base waits for entry of image data (ST41), and then a check is made to determine if the image data is entered (ST42). For instance, if image data is supplied from image data output device $11_i$ to data base $18_l$, along with appendant data, the supplied appendant data is collated with the list stored in image list memory $19_l$ (ST43). If the appendant data and the list do not agree with each other, then it is determined that the image data has been supplied to data base $18_l$ by mistake (ST44). Therefore, data base $18_l$ outputs an error message (ST45), and waits for another input of image data (ST41). The same purpose is achieved by supplying only the appendant data before the image data. In this case, a pre-check is made on the basis of the appendant data.

In the above manner, a data base of the system controls both image data which is mistakenly supplied to it and image data which it should receive but has not yet reached it. As a result, image data never fails to be recorded in an appropriate data base.

Figure 6:
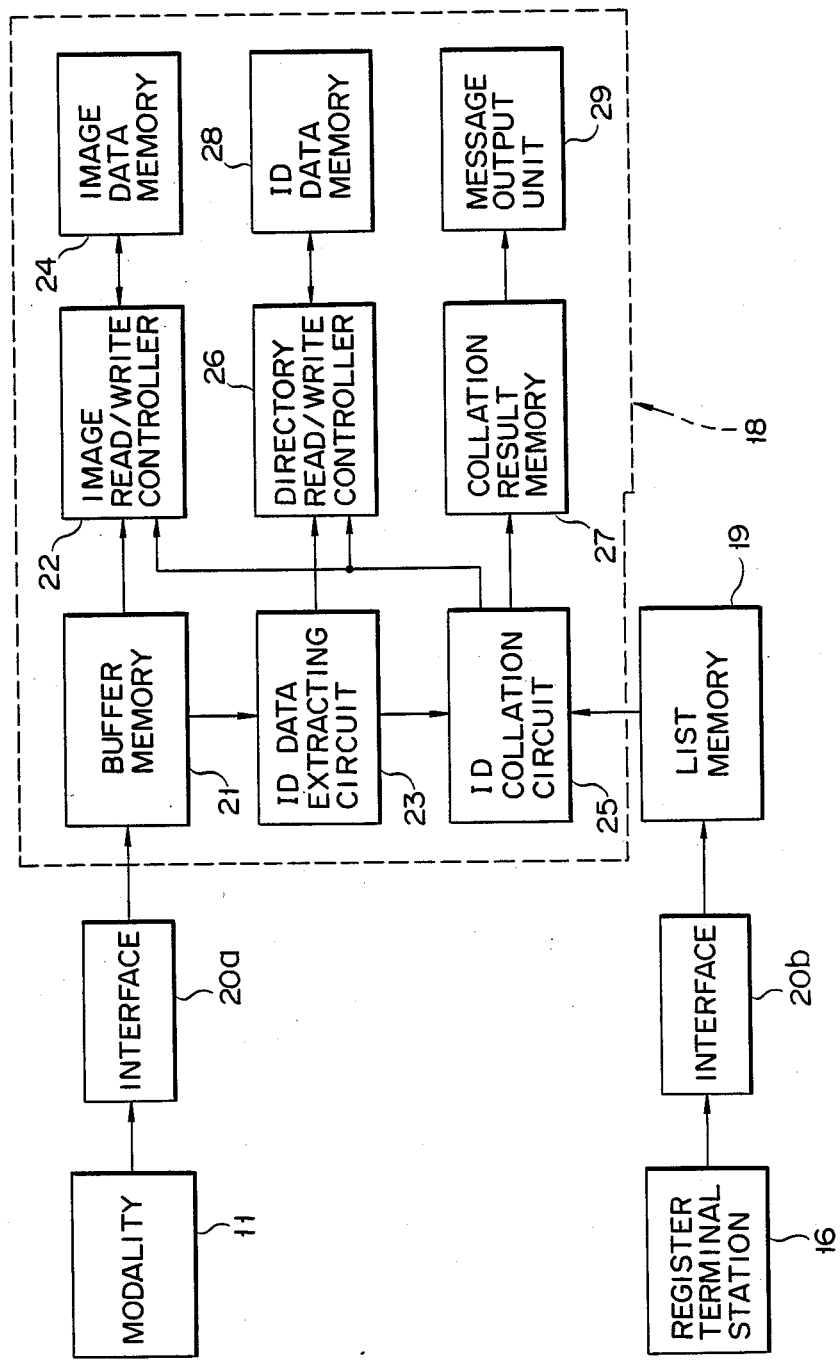
FIG. 6 is a block circuit diagram of the data base.

The construction of a data base will now be described in detail, with reference to FIG. 6.

Each data base 18 includes buffer memory 21 and is connected to list memory 19 which in turn is connected to register terminal station 16, via interface 20b. Buffer memory 21 is connected to image data output section (or modality) 11 via interface 20a. The example shown in FIG. 6 employs only one image data output section 11, in which case interfaces 20a and 20b are provided. In the case where a plurality of image data output sections are employed, a network is employed in the manner shown in FIG. 1, replacing the interfaces.

Buffer memory 21 is connected to both image read/write controller 22 and to ID data extract circuit 23. Image read/write controller 22 is connected to image data memory 24 and controls this memory such that image data can be stored or read out in a reliable manner. ID data extract circuit 23 extracts ID data from the image and appendant data stored in buffer memory 21.

The output terminal of ID data extract circuit 23 is connected to one of the two input terminals of ID collation circuit 25, and also to directory read/write controller 26. Directory read/write controller 26 is connected to ID data memory 28.

The other input terminal of ID collation circuit 25 is connected to the readout terminal of image list memory 19. This memory is connected to register terminal station 16 via interface 20b, as noted above. The output terminal of ID collation circuit 25 is connected to image read/write controller 22, directory read/write controller 26, and collation result memory 27. The readout terminal of collation result memory 27 is connected to message output unit 29.

The operation of the circuits shown in FIG. 6 will now be described. ID data used for identifying a patient is entered from register terminal station 16, on the basis of an examination request form. The ID data includes information sufficient to specify the patient and examination type. For example, it includes the following information: the name of the patient, ID number, the date on which examination is scheduled, the location of examination, and the examination modality. The ID data is supplied, via interface 20b, to list memory 19 for storing.

On the other hand, the image data output from image data output section 11 and the corresponding appendant memory are supplied to buffer memory 21 via interface 20a. The image data and the appendant data are temporarily stored in buffer memory 21. ID data extract circuit 23 extracts ID data from buffer memory 21 and supplies it to ID collation circuit 25. ID collation circuit 25 collates the supplied ID data with that stored in list memory 19. The results of this collation are stored in collation result memory 27. The results indicate one of the following three possibilities:

(1) Appropriate image data was supplied to a data base after ID data was recorded in the list memory;

(2) Inappropriate image data was supplied to the data base by mistake; and (3) Appropriate image data was supplied to the data base before the ID data was recorded in the list memory.

If the ID data corresponding to the supplied image data is stored in list memory 19, i.e., in the case of (1), ID collation circuit 25 supplies a coincidence signal to controllers 22 and 26. In response to the coincidence signal, controllers 22 and 26 permit the image data and ID data to be stored in image data memory 24 and ID data memory 28, respectively.

If the ID data corresponding to the transferred image data is not stored in list memory 19, then either case (2) or case (3) is applied. After a set period of time, therefore, a check is performed once again, to see whether the ID data corresponding to the supplied image data is stored in list memory 19. If, as a result of the second check, it is determined that list memory 19 does not contain such ID data, an error message is output from message output unit 29.

ID collation circuit 25 additionally performs the following function:

At a predetermined time of the day or at regular time intervals, circuit 25 checks the contents of list memory 19. If, as a result, it is found that there is image data which has not yet reached the data base, an error message is output from message output unit 29. Specifically, this error message is output in the following two cases:

(A) Appropriate image data has not yet reached the data base. (Although the ID data corresponding to the image data is stored in list memory 19, the image data itself has not yet reached the data base after a predetermined period.)

(B) Inappropriate image data has been supplied to the data base. (The ID data corresponding to the supplied image data is not recorded in list memory 19.)

In the above embodiment, the ID data is entered in an off-line manner. However, if an ordering system is employed for making an examination request, it can be interfaced directly with the system located at the examination department. In the above embodiment, only one image data output section 11 is connected to interface 20a. However, if a network is employed, the data base can be interfaced with a plurality of image data output sections.

Figure 7:
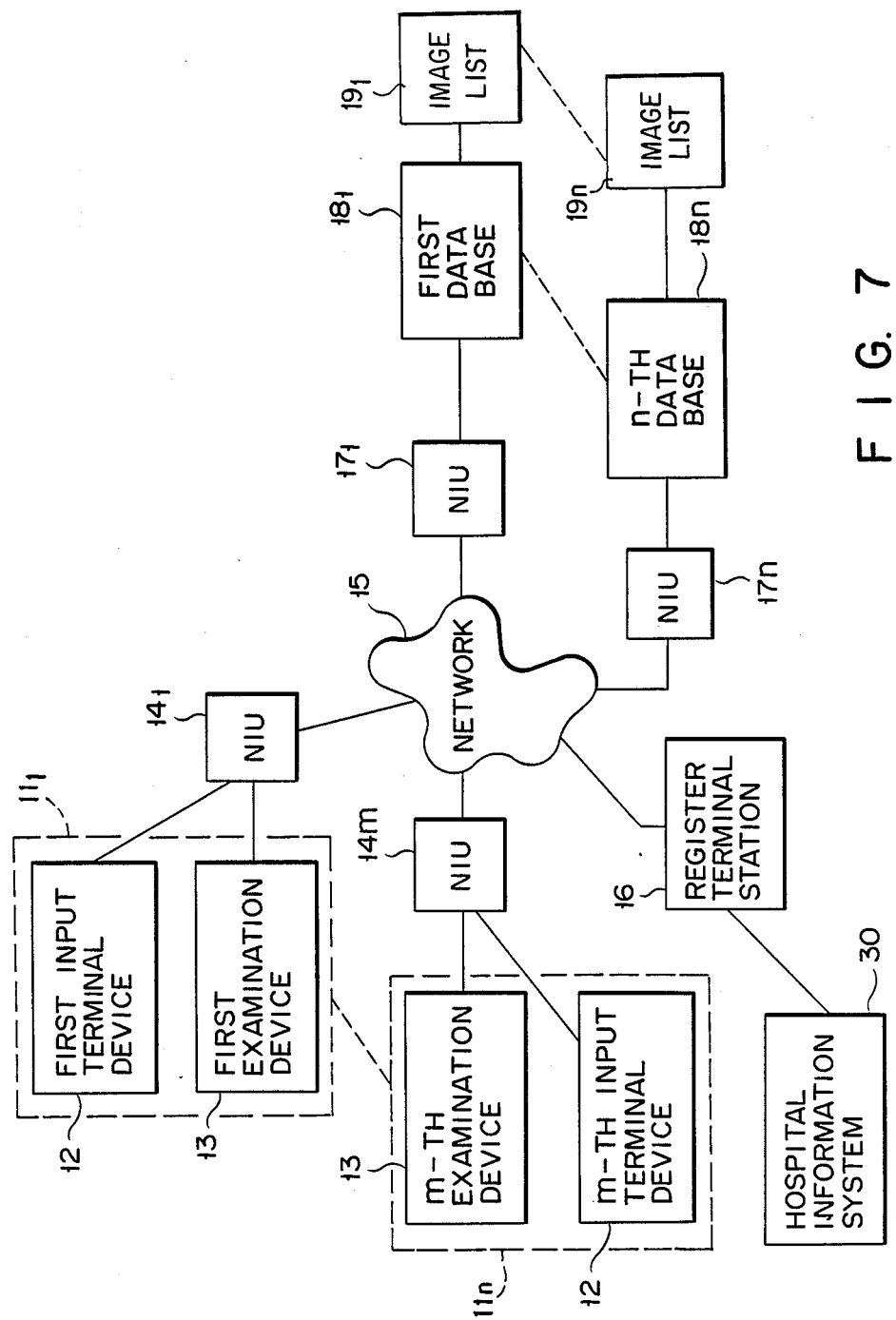
FIG. 7 illustrates the construction of an on-line picture archiving and communication system according to another embodiment of the present invention.

Furthermore, the present invention is applicable to an on-line system. According to this on-line system, as shown in FIG. 7, hospital information computer 30 (which controls information, in various categories, relating to one or a number of hospitals) is connected to register terminal station 16, and information relating to a patient is entered from computer 30 alone. The data necessary for the recording of image data is extracted from the information entered from computer 30. On the basis of the extracted data, a register list is prepared at each data base.

What is claimed is:

1. A picture archiving and communication system, comprising:
   at least one data output means for outputting image data and appendant data, the appendant data including at least specific data used for specifying or identifying the image data and destination data representing where the image data should be sent;
   at least one terminal means from which specific data used for specifying or identifying image data and destination data are entered independently of the appendant data output from said at least one data output means; and
   at least one data base means for receiving image data from said at least one data output means, each of said at least one data base means including means for preparing a register list containing at least specific data and destination data entered from said at least one terminal means and corresponding to the image data to be received by said at least one data base means.

2. A picture archiving and communication system according to claim 1, wherein each of said at least one data base means is arranged in a corresponding diagnosis department of a hospital in which said picture archiving and communication system is being used.

3. A picture archiving and communication system according to claim 1, wherein each of said at least one data output means includes imaging means for deriving an image of a patient of a hospital in which said picture archiving and communication system is being used and for outputting the image data in accordance with the derived image, and data input means for entering and outputting the appendant data including the specific data and the destination data.

4. A picture archiving and communication system according to claim 3, wherein the specific data entered by each data input means includes an ID code identifying the image data outputted by the imaging means included in the corresponding data output means, the patient,s name, an ID code identifying the patient, the patient's date of birth, the type of imaging means included in the corresponding data output means, a hospital examination department in which the corresponding data output means is located, and the name of a hospital clinician requesting than an image of the patient be derived, and wherein the destination data entered by each data input means includes a hospital diagnosis department from which the clinician is requesting that the image of the patient be derived.

5. A picture archiving and communication system according to claim 1, wherein said at least one terminal means allows the specific data and the destination data to be entered in an off-line manner.

6. A picture archiving and communication system according to claim 1, wherein said at least one terminal means allows the specific data and the destination data to be entered in an on-line manner.

7. A picture archiving and communication system according to claim 1, wherein the register list preparing means of each of said at least one data base means includes means for detecting whether or not the corresponding register list is filled with data, means for collating the specific data output by said at least one data output means with the specific data in the corresponding register list, and means for deleting from the corresponding register list any specific data which is collated with any of the specific data output by said at least one data output means and any other data, including destination data, which is associated with the collated specific data is the register list is full.

8. A picture archiving and communication system, comprising:

at least one data output means for outputting image data and appendant data, the appendant data including at least specific data used for specifying or identifying the image data and destination data representing where the image data should be sent;

at least one terminal means from which specific data used for specifying or identifying image data and destination data are entered independently of the appendant data output from said at least one data output means; and at least one data base means for receiving image data from said at least one data output means, each of said at least one data base mans including means for preparing a register list containing at least specific data and destination data entered from said at least one terminal means and corresponding to the image data to be received by said at least one data base means, means for collating the specific data and the destination data output by said at least one data output means with that in the corresponding register list, and a data base which stores the image data received from said at least one data output means, wherein said data base stores only image data which is identified by specific data and destination data which are collated with that in the corresponding register list.

9. A picture archiving and communication system according to claim 8, wherein each of said at least one data base means further includes means for outputting an error message if the corresponding collating means detects disagreement between the specific data and the destination data output at least one data output means and that in the corresponding register list.

10. A picture archiving and communication system according to claim 8, wherein the collating means of each of said at least one data base means detects whether or not the corresponding image data received from said at least one data output means is identified by any of the specific data and the destination data in the corresponding register list.

11. A picture archiving and communication system according to claim 10, wherein each of said at least one data base means further includes memory means used for storing results of the collation carried out by the corresponding collating means.

12. A picture archiving and communication system according to claim 10, wherein if the collating means of each of said at least one data base means detects that the corresponding image data received from said at least one data output means is not identified by any of the specific data and the destination data in the corresponding register list, it once again collates the specific data and the destination data output by said at least one data ouput means with that in the corresponding register list after a certain period of time.

13. A picture archiving and communication system according to claim 8, wherein the collating means of each of said at least one data base means checks the corresponding register list at a predetermined time or at regular time intervals, and if it detects that image data which is identified by the specific data and the destination data in the corresponding register list has not yet been received from said at least one data output means, it outputs an error message.

14. A picture archiving and communication system according to claim 8, wherein said at least one data output means, said at least one terminal means, and said at least one data base means are connected to one another by means of a network.

15. A picture archiving and communication system according to claim 8, wherein each of said at least one data output means includes at least one of an X-ray photography device, an ultrasonic imaging device, an NMR imaging device, a nuclear medical device, an X-ray CT device, and an electronic endoscope device.

16. A picture archiving and communication system according to claim 8, wherein each of said at least one data output means includes a device for outputting information relating to a living body, such as an electrocardiogram or an electrocorticogram.

17. A picture archiving and communication system according to claim 8, wherein the picture archiving and communication system is being used in a hospital, wherein the specific data entered from each of said at least one terminal means includes the name of a hospital clinician requesting an examination of a hospital patient, and wherein the corresponding destination data entered from each of said at least one terminal means includes a hospital diagnosis department from which the clinician is requesting the examination.

* * * * *